(12) United States Patent
Bernier et al.

(10) Patent No.: US 12,358,032 B2
(45) Date of Patent: Jul. 15, 2025

(54) MEAT INJECTION NEEDLES CLEANING APPARATUS

(71) Applicant: Groupe CFR, Sainte-Claire (CA)

(72) Inventors: Laurent Bernier, Quebec (CA); Jerome Rodrigue-Labrecque, Buckland (CA); Mario Langlois, Sainte-Claire (CA)

(*) Notice: Subject to any disclaimer, the term of this patent is extended or adjusted under 35 U.S.C. 154(b) by 74 days.

(21) Appl. No.: 17/978,340

(22) Filed: Nov. 1, 2022

(65) Prior Publication Data

US 2023/0234108 A1  Jul. 27, 2023

Related U.S. Application Data

(60) Provisional application No. 63/302,875, filed on Jan. 25, 2022.

(51) Int. Cl.
| | | |
|---|---|---|
| *B08B 9/032* | (2006.01) | |
| *A61L 2/025* | (2006.01) | |
| *A61L 2/04* | (2006.01) | |
| *A61L 2/10* | (2006.01) | |
| *A61L 2/24* | (2006.01) | |

(52) U.S. Cl.
CPC ........... *B08B 9/0323* (2013.01); *A61L 2/025* (2013.01); *A61L 2/04* (2013.01); *A61L 2/10* (2013.01); *A61L 2/24* (2013.01)

(58) Field of Classification Search
CPC . B08B 9/032; A61L 2/025; A61L 2/04; A61L 2/10; A61L 2/24; A61L 2202/17; A61L 2202/24; Y02A 40/90
See application file for complete search history.

(56) References Cited

U.S. PATENT DOCUMENTS

| | | |
|---|---|---|
| 2,958,332 A | 11/1960 | Schueler |
| 3,900,339 A | 8/1975 | Filipin et al. |
| 4,419,141 A | 12/1983 | Kunkel |
| 5,363,867 A | 11/1994 | Kawano et al. |
| 5,378,287 A | 1/1995 | Pedziwiatr |
| 5,567,246 A | 10/1996 | Bowden |
| 5,935,411 A | 8/1999 | Brown et al. |
| 6,082,377 A | 7/2000 | Frey |
| 6,302,123 B1 | 10/2001 | Wilson |
| 10,286,427 B2 | 5/2019 | Vasquez et al. |
| 10,973,237 B2 | 4/2021 | Lagares Corominas |

(Continued)

FOREIGN PATENT DOCUMENTS

| | | | |
|---|---|---|---|
| CN | 106137443 B | 11/2016 | |
| CN | 108636913 A | * 10/2018 | ............. B08B 13/00 |

(Continued)

OTHER PUBLICATIONS

CN-212883955-U Written Description (Year: 2021).*

(Continued)

*Primary Examiner* — Jason Y Ko
(74) *Attorney, Agent, or Firm* — Benoit&Cote Inc.; Mathieu Audet

(57) ABSTRACT

A meat injection needles cleaning apparatus comprising a washing stage for washing the exterior of the needles, an injection stage for injecting water and air in the needles, an ultraviolet stage for disinfecting the needles and an ultrasonic stage for cleaning the needles. A method of cleaning thereof is also contemplated by the present application.

21 Claims, 17 Drawing Sheets

(56) References Cited

U.S. PATENT DOCUMENTS

| | | | |
|---|---|---|---|
| 2004/0129299 | A1 | 7/2004 | Kocherlakota et al. |
| 2005/0000550 | A1 | 1/2005 | Fick et al. |
| 2011/0132404 | A1 | 6/2011 | Lutz |
| 2011/0290034 | A1 | 12/2011 | McDonnell et al. |
| 2013/0306117 | A1* | 11/2013 | Yamazaki .............. B08B 9/00 134/171 |
| 2015/0328395 | A1 | 11/2015 | Zhao |
| 2016/0101423 | A1* | 4/2016 | Smith ............... B08B 9/0323 134/169 R |
| 2017/0296030 | A1* | 10/2017 | VanderRoest ....... A47L 15/4409 |
| 2018/0289446 | A1* | 10/2018 | Vasquez ................. B08B 11/02 |
| 2018/0295845 | A1* | 10/2018 | Lagares Corominas ................... A23B 4/285 |

FOREIGN PATENT DOCUMENTS

| | | | |
|---|---|---|---|
| CN | 209577559 | | 11/2019 |
| CN | 211367824 | | 8/2020 |
| CN | 211914765 | | 11/2020 |
| CN | 212883955 | | 4/2021 |
| CN | 212883955 | U * | 4/2021 |
| CN | 213480768 | | 6/2021 |
| CN | 214865849 | | 11/2021 |
| CN | 215465697 | | 1/2022 |
| GB | 1314633 | A | 4/1973 |
| JP | 2002277450 | A * | 9/2002 |
| WO | 2003076088 | | 9/2003 |

OTHER PUBLICATIONS

CN-108636913-A Written Description (Year: 2018).*

JP-2002277450-A Written Description (Year: 2002).*

Fomaco Automatic Needle Cleaner—Apr. 3, 2020, YouTube; https://www.youtube.com/watch?v=kde3jv3ipU4.

Needle cleaning machine—Needle Care; Dec. 31, 2021, https://roser-group.com/en/product/needle-cleaning-machine-needle-care/.

Needleclean—Metalquimia; Automatic cleaning and sanitation of needles; 4 pages; Jun. 18, 2021, https://www.metalquimia.com/en/machinery/filters-and-accessories/needleclean-16/.

Automatic Cleaning and Sanitation of Needles, Metalquimia_Needleclean_eBook, Jan. 9, 2018, 4 pages.

Needlebed washing machine H2G—SHIMA SEIKI and STOLL demonstration, Feb. 25, 2016, https://www.youtube.com/watch?v=iTSb2VbO7bY.

MEPSCO UltraCAT Dual Head Injector, 2 pages, Dec. 31, 2021.

* cited by examiner

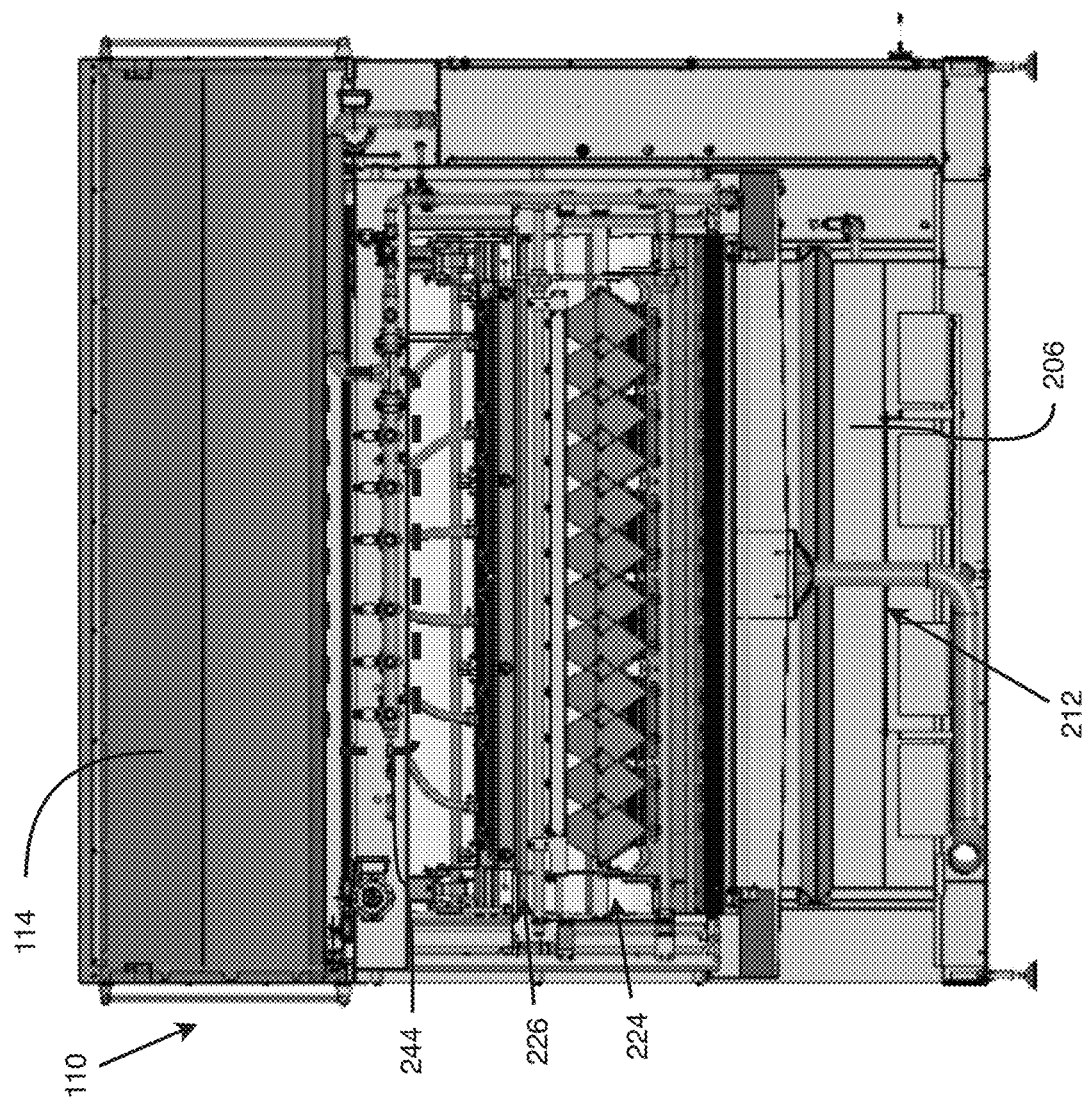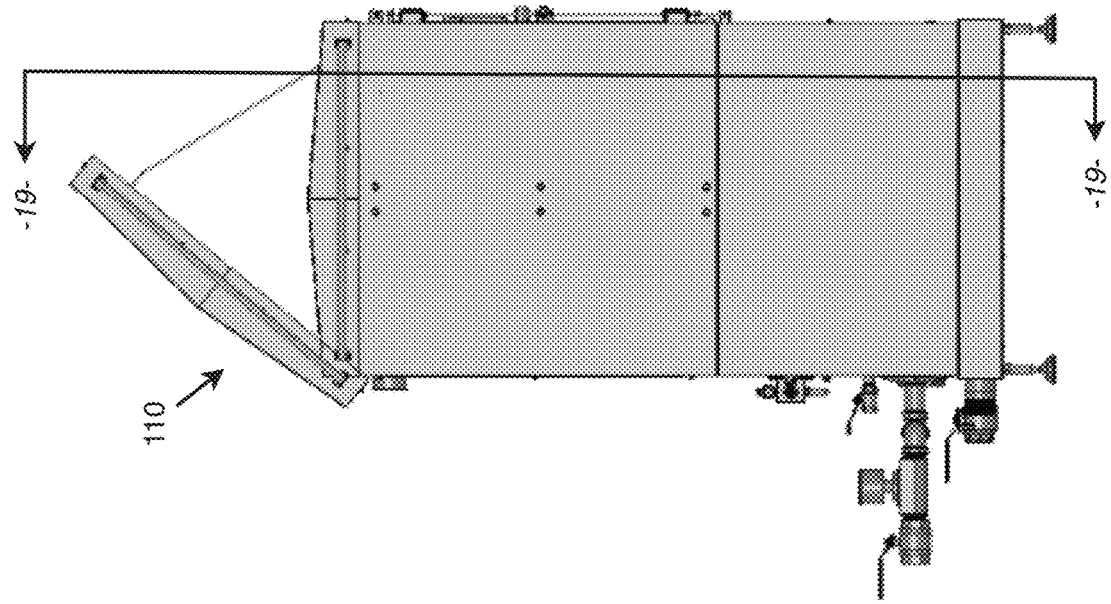

MEAT INJECTION NEEDLES CLEANING APPARATUS

CROSS-REFERENCE TO RELATED APPLICATION

This application relates to and is a non-provisional application claiming priority under 35 U.S.C. § 119(e) from U.S. patent application Ser. No. 63/302,875, filed Jan. 25, 2022, under 35 U.S.C. § 111, entitled MEAT INJECTION NEEDLES CLEANING APPARATUS, the specification of which is hereby incorporated herein by reference in its entirety.

BACKGROUND

(A) Field

This invention relates generally to meat injection needles cleaning apparatuses. The present invention more specifically relates to methods and apparatuses for cleaning needles used for injecting meat with liquid or else.

(b) Related Prior Art

Meat can be injected with salt water or other liquid substances for various reasons known in the art. A plurality of needles is used to puncture the meat and inject the liquid therein. Needles are currently cleaned individually.

It is therefore desirable to provide an apparatus to batch clean the needles.

Other deficiencies and opportunities will become apparent to one skilled in the art to which the invention pertains in view of the following summary and detailed description with its appended figures.

SUMMARY

It is one aspect of the present invention to alleviate one or more of the shortcomings of background art by addressing one or more of the existing needs in the art.

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

The invention is generally described as a method, a system, a device and/or an apparatus for batch cleaning meat injection needles.

Aspects of our work provide, in accordance with at least one embodiment thereof, a method and apparatus for washing the needles' exterior.

At least one aspect of the instant invention provides, in accordance with at least one embodiment thereof, a method and apparatus for washing the needles' interior.

At least one aspect of the instant invention provides, in accordance with at least one embodiment thereof, a method and apparatus for drying the needles' interior.

Moreover, at least one other aspect of the instant invention provides, in accordance with at least one embodiment thereof, a method and apparatus for disinfecting the needles' exterior with ultraviolet light.

In at least one aspect of the instant invention provides, in accordance with at least an embodiment thereof, a method and apparatus for cleaning the needles with ultrasonic waves.

At least one other aspect of the present invention provides, in accordance with at least an embodiment thereof, a method and apparatus for washing the needles' exterior.

In some aspects, the techniques described herein relate to a meat injection needles cleaning apparatus for cleaning needles from residues, the needles having an exterior surface, the apparatus including: a housing defining a closeable room including a bath for containing a soaking liquid, and elevated area outside the bath; a support for mounting the needles thereto; support driving assembly for driving the support in the housing between a) a soaking position where the needles soak in the soaking liquid, and b) at least one elevated position in the elevated area; cleaning assembly for cleaning the needles when they are in the elevated area, wherein cleaning the needles includes at least one of a) spraying the exterior surface of the needles with one of a cleaning liquid or water, and b) injecting the needles with one of the cleaning liquid or water; and a movable lid movable between a) a cover position where the movable lid isolates the bath from residues, the cleaning liquid, and water from the elevated area, and b) an open position wherein the bath is open for the support to enter therein.

In some aspects, the techniques described herein relate to a meat injection needles cleaning apparatus adapted for cleaning needles from residues, the needles having an exterior surface, the apparatus including: a bath for containing a soaking liquid; cleaning assembly for cleaning the needles, wherein cleaning the needles includes at least one of a) spraying the exterior surface of the needles with one of a cleaning liquid or water, and b) injecting the needles with one of the cleaning liquid or water; ultrasound emitters for emitting ultrasonic waves to be transmitted to the needles through the soaking liquid of the bath; ultraviolet light emitters for submitting the needles to ultraviolet light; and controller for selectively activating the cleaning assembly, the ultrasound emitters, and the ultraviolet light emitters.

In some aspects, the techniques described herein relate to a method for cleaning needles having an exterior surface from residue, the method including: having the needles mounted to a movable support of an apparatus; having the needles in an elevated area of the apparatus separated from a bath containing soaking liquid; cleaning the needles through at least one of a) spraying the exterior surface of the needles with one of a cleaning liquid or water, and b) injecting the needles with one of the cleaning liquid or water, wherein cleaning the needles is performed with a lid closed, the lid isolating the elevated area from the bath; opening a lid and moving the support in a soaking position where the needles are in the bath; cleaning the needles by emitting ultrasonic waves in the bath; moving the support out of the bath and closing the lid; repeating the step of cleaning the needles through at least one of a) spraying the exterior surface of the needles with one of the cleaning liquid or water, and b) injecting the needles with one of the cleaning liquid or water, wherein the lid is movable between a) a cover position where the lid prevents residues and the cleaning liquid to travel from the elevated area to the bath, and b) an open position wherein the bath is open for the support to enter therein.

Additional and/or alternative features, aspects, and advantages of embodiments of the present invention will become apparent from the following description, the accompanying drawings, and the appended claims.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which:

FIG. 3 is a front elevation view of the needles cleaning apparatus with a lower part of the housing depicted, FIG. 3 illustrating internal components of the cleaning apparatus of FIG. 1 with the needle block support at a second position and a third position;

FIG. 4 is a front elevation view of the needles cleaning apparatus with a lower part of the housing depicted, FIG. 4 illustrating internal components of the cleaning apparatus of FIG. 1 with the needle block support at a third position;

FIG. 18 is a side elevation view of a needle cleaning apparatus in accordance with an embodiment;

FIG. 19 is a cross-section front elevation view of the needles cleaning apparatus according to cross-section line 19-19 of FIG. 18.

It will be noted that throughout the appended drawings, like features are identified by like reference numerals.

DETAILED DESCRIPTION

The realizations will now be described more fully hereinafter with reference to the accompanying figures, in which realizations are illustrated. The foregoing may, however, be embodied in many different forms and should not be construed as limited to the illustrated realizations set forth herein. It may be evident, however, that the present invention may be practiced without these specific details. In other instances, when applicable, well-known structures and devices are shown in block diagram form in order to facilitate describing the present invention.

The features provided in this specification mainly but might not exclusively relate to principles of apparatuses or other machines adapted to clean needles used for meat injection.

With respect to the present description, references to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values and of values herein or on the drawings are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described realizations. The use of any and all examples, or exemplary language ("e.g.," "such as," or the like) provided herein, is intended merely to better illuminate the exemplary realizations and does not pose a limitation on the scope of the realizations. No language in the specification should be construed as indicating any unclaimed element as essential to the practice of the realizations.

In the following description, it is understood that terms such as "first", "second", "top", "bottom", "above", "below", and the like, are words of convenience and are not to be construed as limiting terms.

Figure 1:
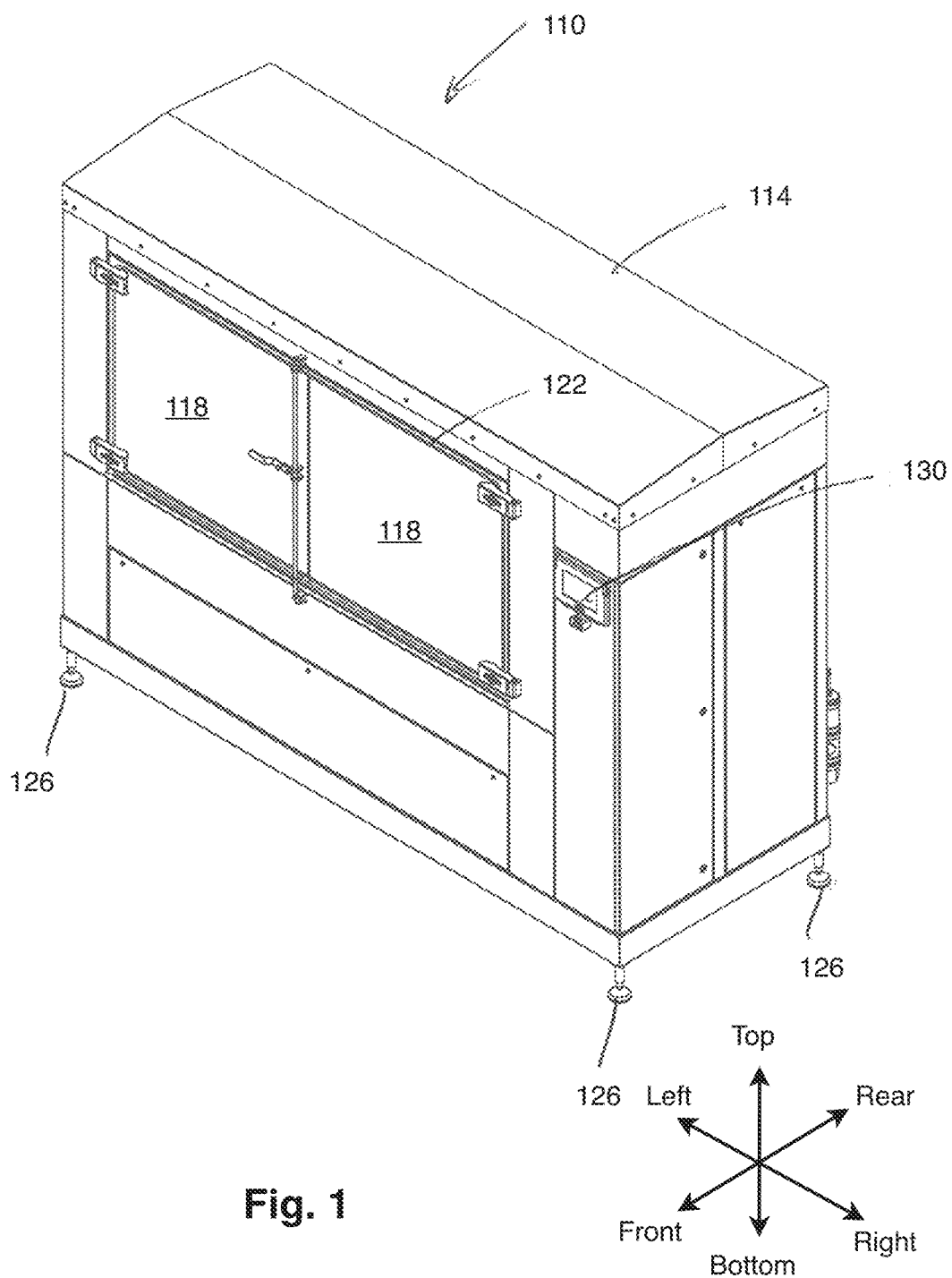
FIG. 1 is an perspective view of a needles cleaning apparatus.

The terms "top", "up", "upper", "bottom", "lower", "down", "vertical", "horizontal", "interior" and "exterior" and the like are intended to be construed in their normal meaning in relation with normal installation of the product, with indication of normal orientation of the components being provided on FIG. 1.

Figure 2:
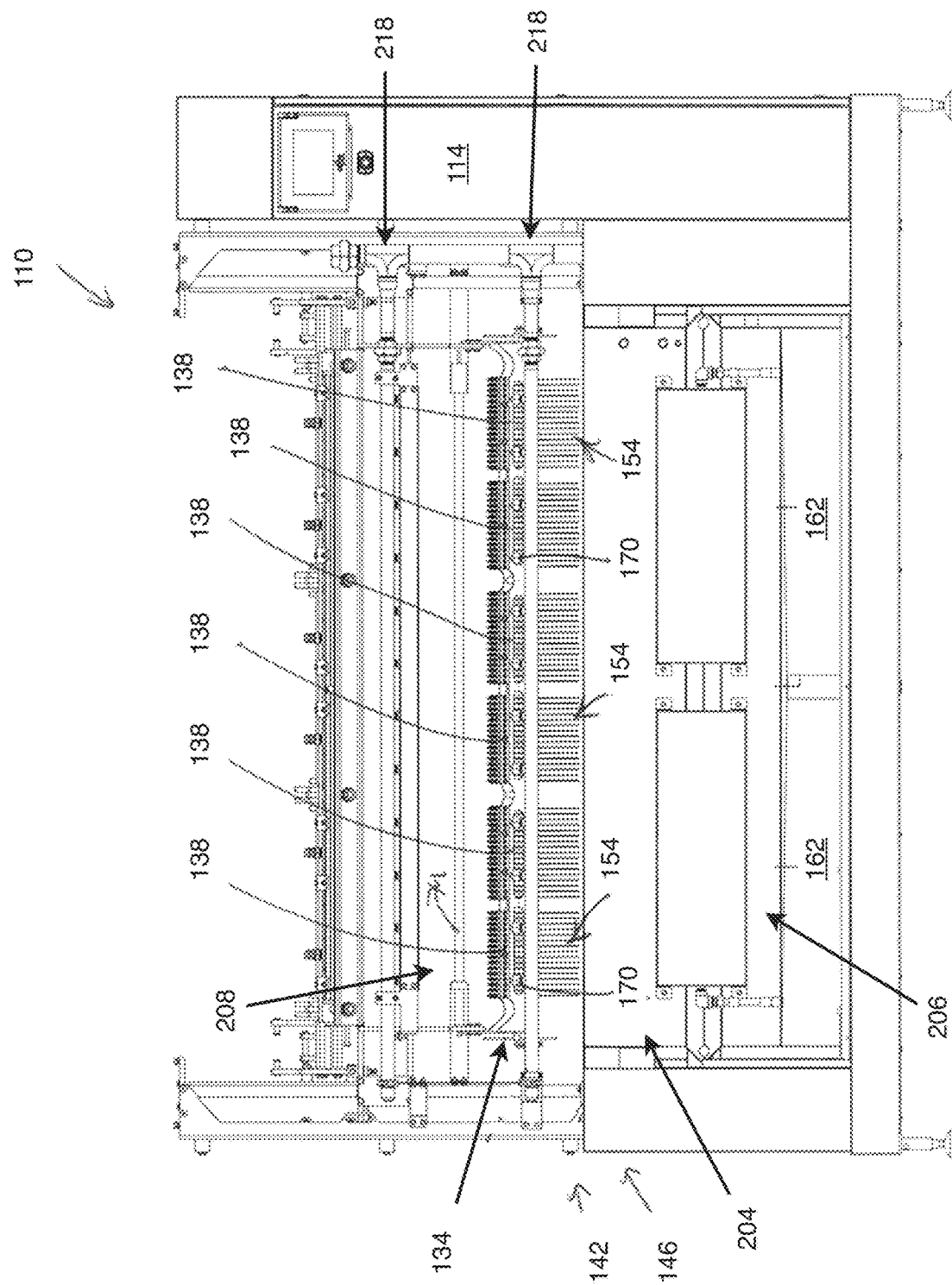
FIGS. 2 to 4 is a front elevation view of the needles cleaning apparatus with a lower part of the housing depicted, FIG. 2 illustrating internal components of the cleaning apparatus of FIG. 1 with the needle block support at a first position.

Referring now to the drawings, and more particularly to FIGS. 1 and 2, a cleaning apparatus 110 comprises a housing 114 and a pair of pivotable doors 118 mating with the housing 114 with a gasket portion 122 to define a closeable cleaning room 204 divided between a bath 206 and an elevated area 208 elevated relative to the bath 206. The housing 114 is equipped with a set of adjustable legs 126 to stand in a location, and an external control display 130, operably connected to a controller 232, FIG. 17, controlling the cleaning process, for an operator to operate the cleaning apparatus 110.

FIG. 2 depicts the cleaning apparatus 110 with no top, no doors 118 and a front plate removed to show internal components of the cleaning apparatus 110, including the closeable cleaning room 204 comprising the bath 206 and the elevated area 208. The cleaning apparatus 110 comprises a needle block support 134 adapted to secured thereon preferably a plurality of needle blocks 138. The needle block support 134 is mounted to a support driving assembly 222, FIG. 7, configured to lower and raise the needle block support 134 between at least three positions.

Figure 3:
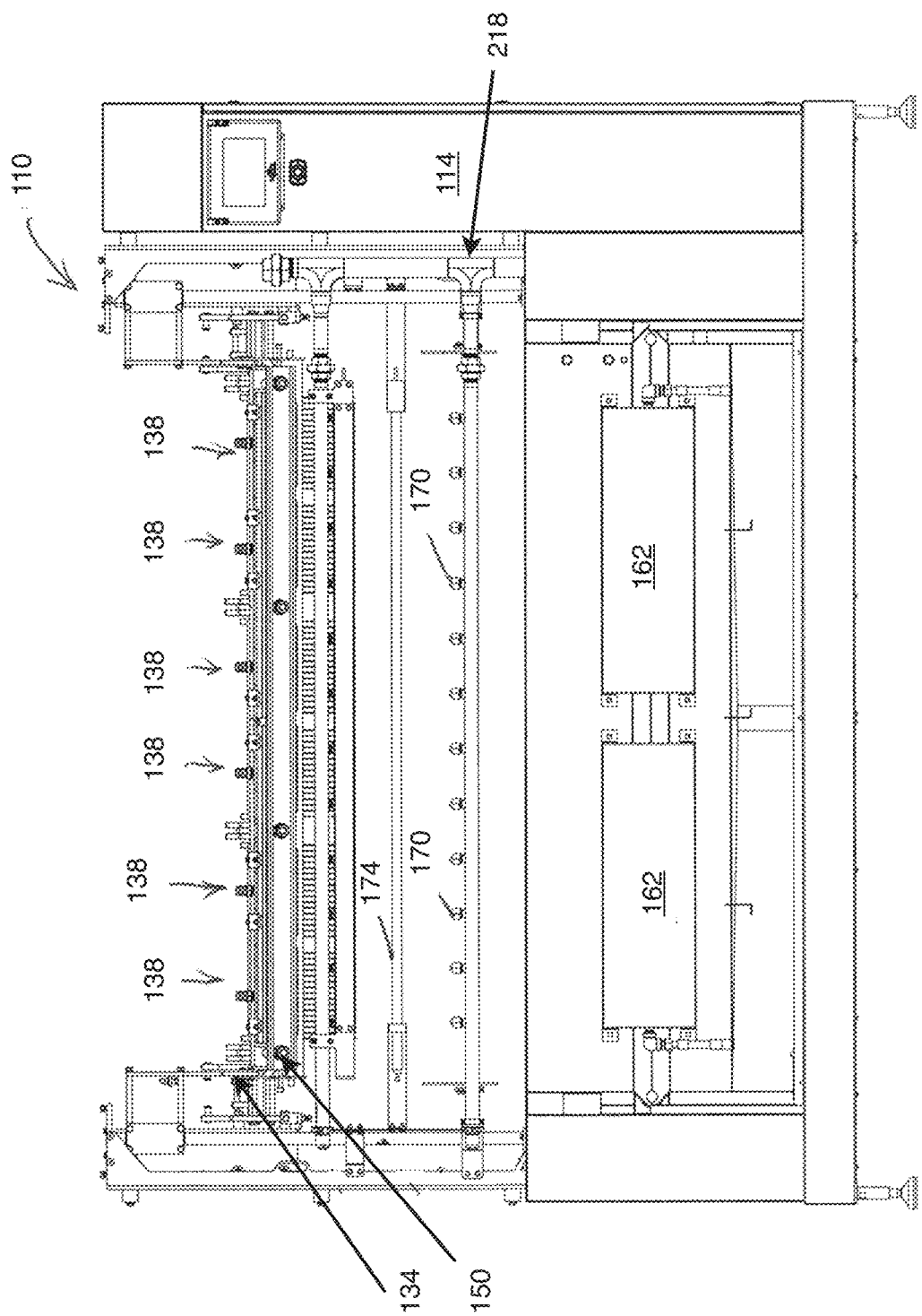
Figure 4:
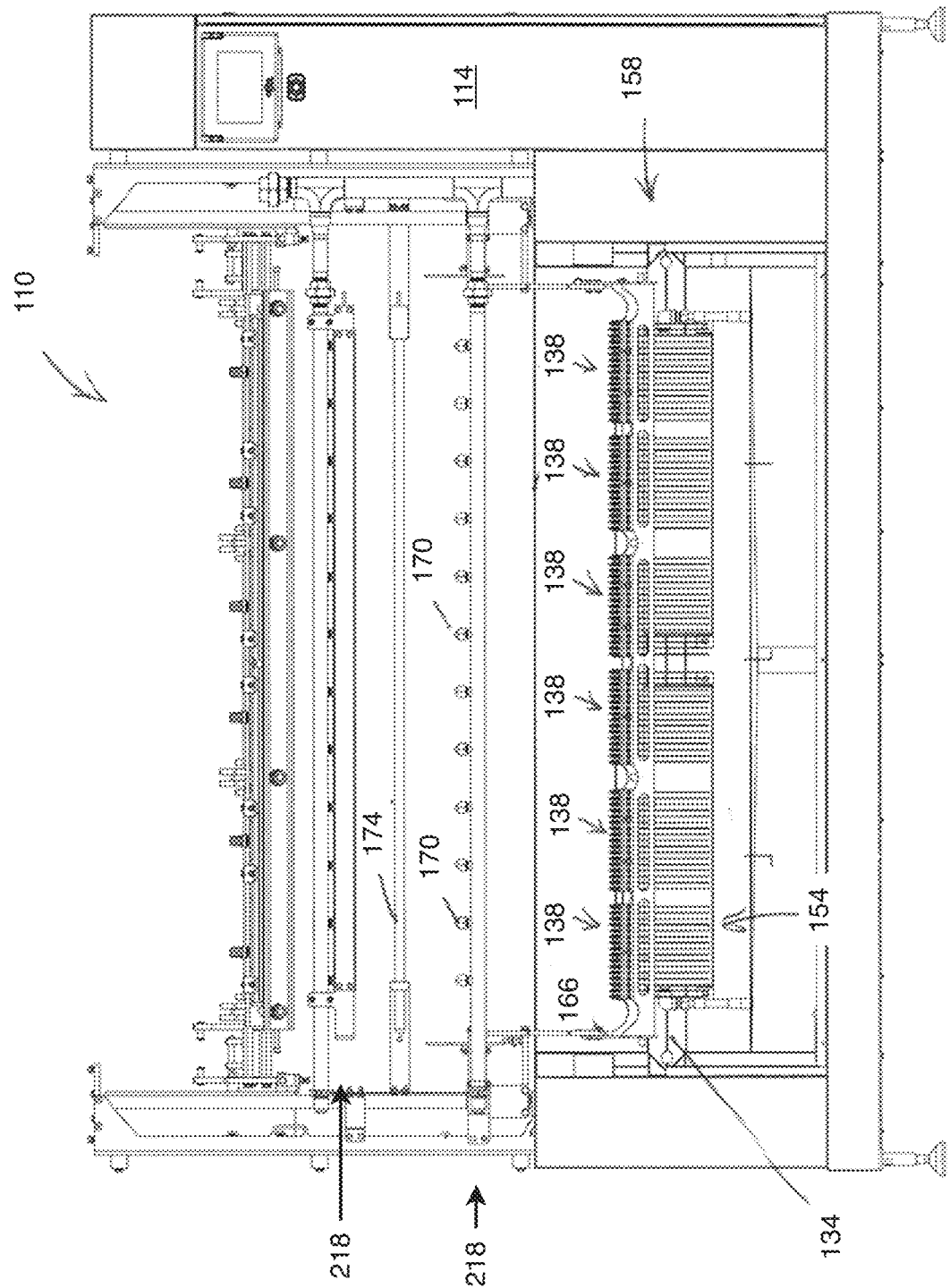
Figure 5:
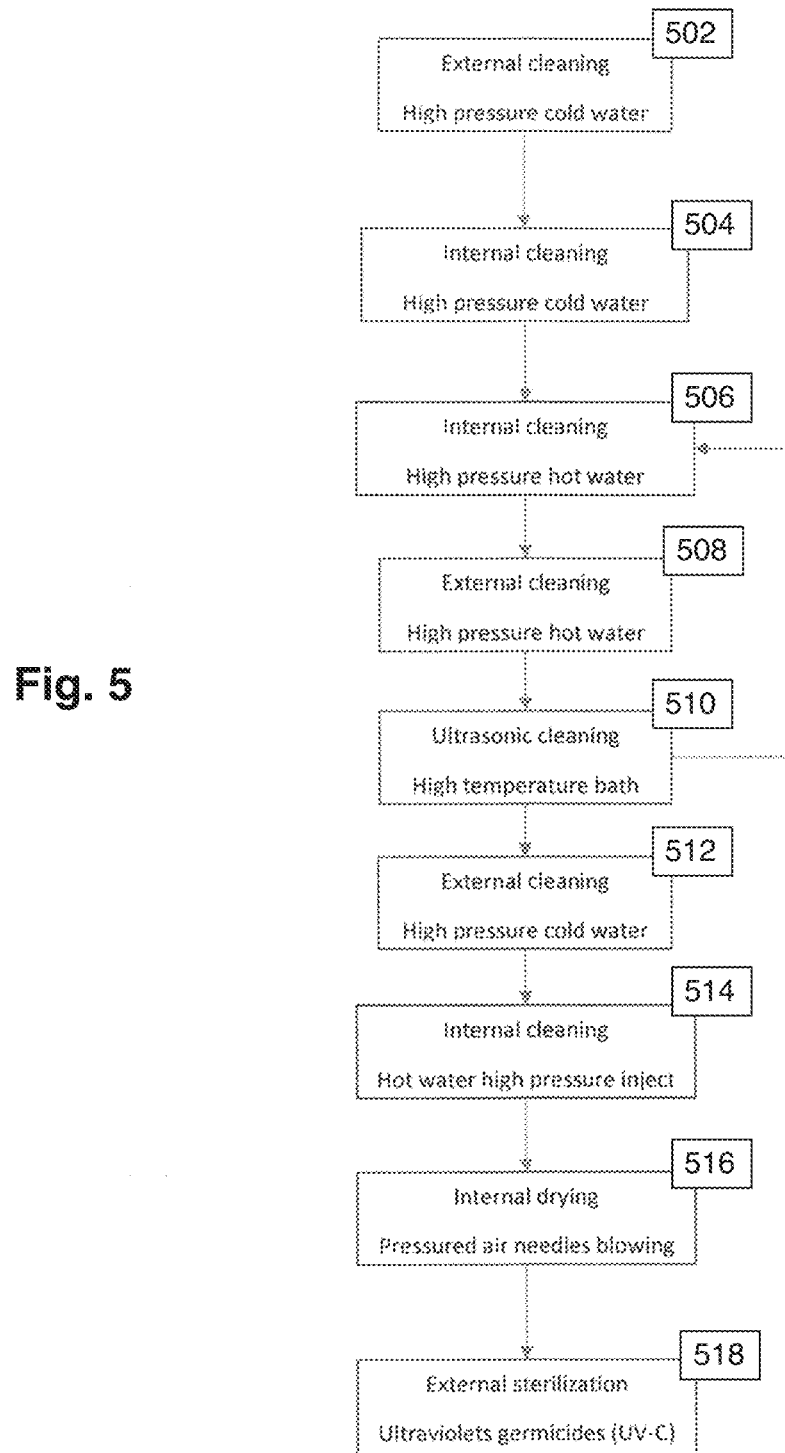
FIG. 5 is a flow chart illustrating an exemplary series of steps for a process of cleaning needles.

Referring now to FIG. 5, and in support to FIGS. 2 to 4, it is depicted an exemplary flow chart of a typical series of steps for cleaning the needles 154 mounted to the needle block support 134. Not illustrated, the method begins with mounting the needles 154 to the needle block support 134, located at the time at an elevation corresponding, in a preferred realization, to the elevation of the opening closable with the pivotable doors 118. The mounting step comprises to install the needle blocks 138 and lock them in place. Once mounted, and the doors 118 closed, the cleaning process can be initiated.

According to an exemplary embodiment, the needle cleaning process begins with step 502 of spraying the exterior of the needles 154 with high pressure cold cleaning liquid, e.g., water. This step may involve raising and lowering in a repetitive manner the needle block support 134 in front of the nozzles 170 for the high-pressure jets of cleaning liquid to reach the exterior surface of the needles 154 over their whole height. It is to be noted that at this step, the lid 210 dividing the elevated area 208 from the bath 206 is closed thereby having the cleaning liquid of the jets and the residues dislodged from the needles 154 falling on the lid 210, FIG. 16, and redirected in the gutter assembly 212, FIG. 16, through which the cleaning liquid and residues are directed to an outlet 214, FIG. 16.

Figure 10:
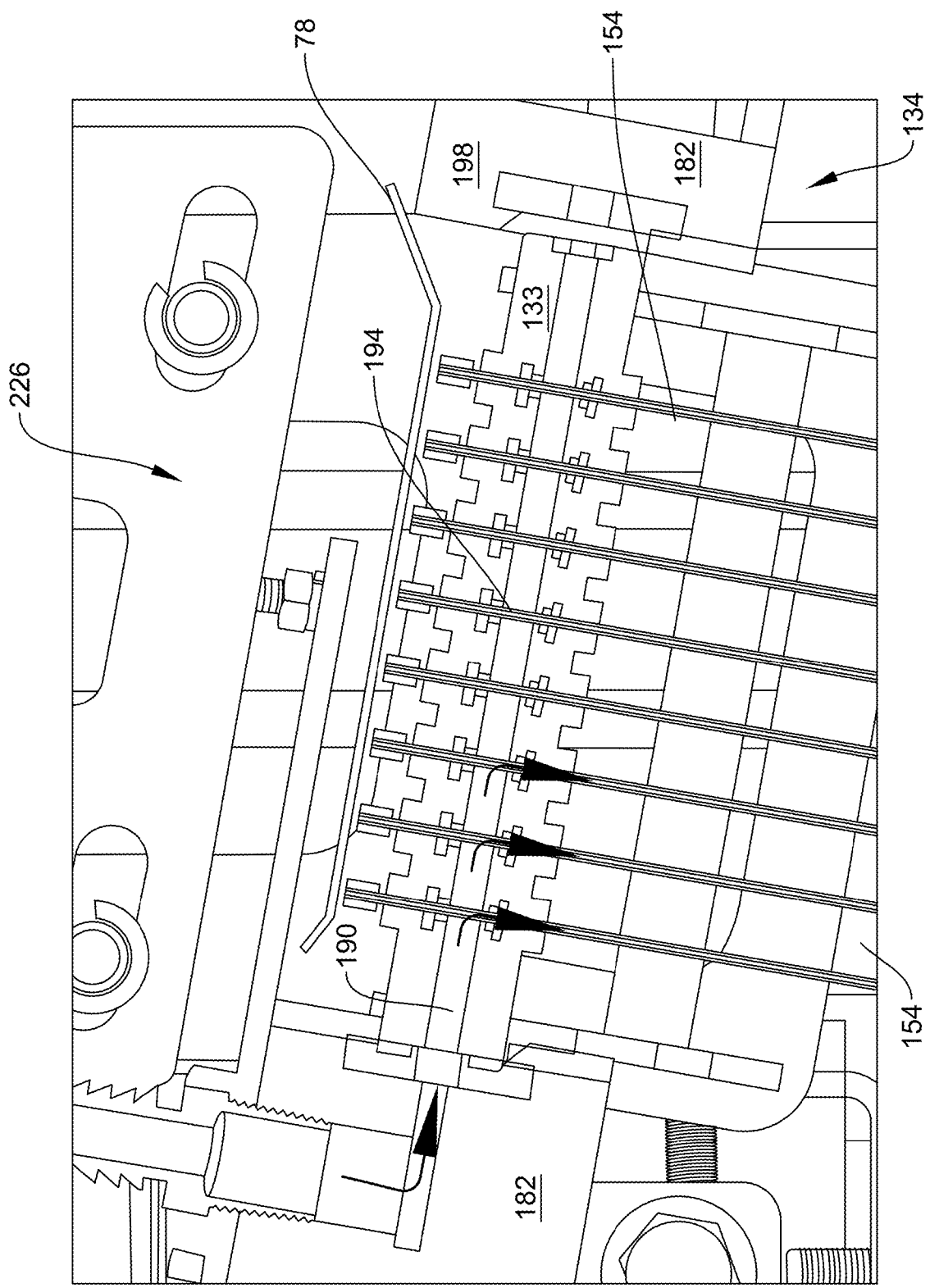
FIGS. 10 and 11 are a close-up cross-section view depicting a needle block with liquid low indication when the injection assembly operating on the needle block.
Figure 11:
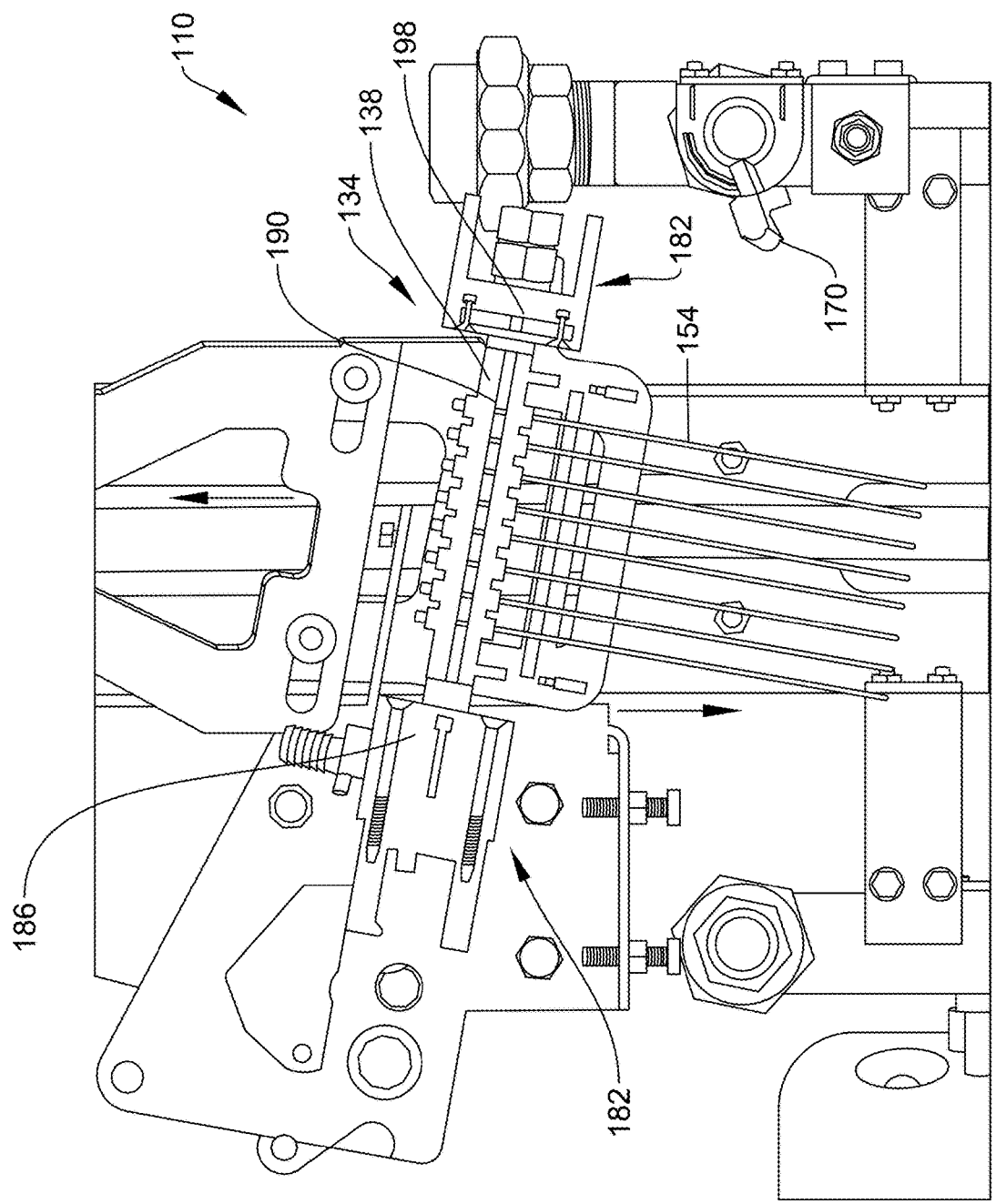
Figure 12:
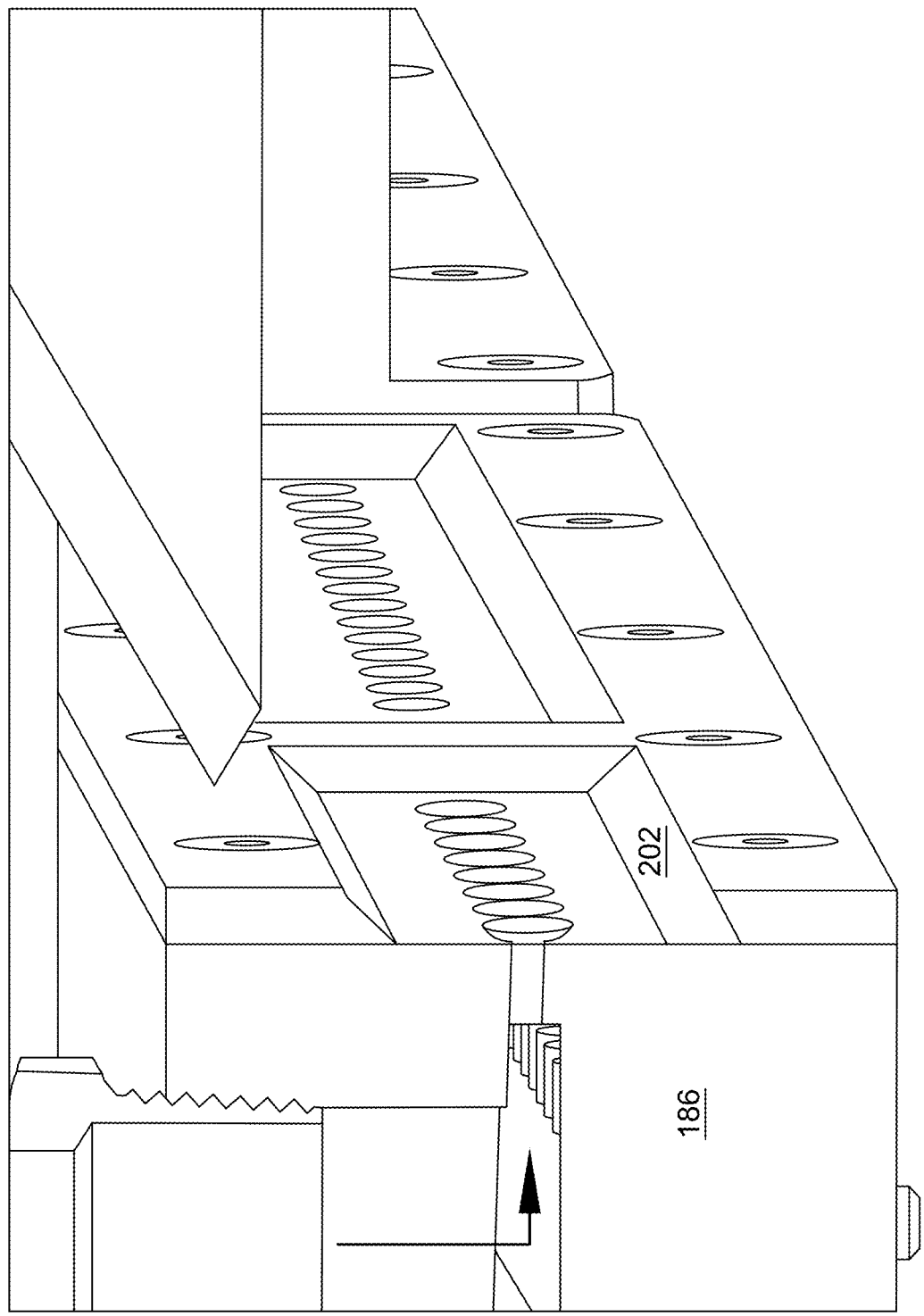
FIG. 12 is a close-up cross section view depicting a needle block mating surface of an injection assembly in accordance with an embodiment.

Step 504 comprises to raise the needle block support 134 to mate the injection assembly 226, FIG. 10, for cleaning the interior of the needles 154 by injecting high-pressure cold cleaning liquid, e.g., water, in the needles 154. According to a preferred realization, the injection assembly 226 is adapted with controllable valves 244, FIG. 19, to sequentially inject cleaning liquid in needle blocks 138 one after the other. Cleaning liquid and residues dislodged from the interior of the needles 154 also fall over the lid 210, redirected into the gutter assembly 212 and ultimately led to an outlet 214.

According to embodiments, steps 502 and 504 may be repeated with cold cleaning/rinsing liquid, cold water, hot cleaning liquid or hot water. FIG. 5 depicts the method with steps 502 and 504 followed with steps 506 and 508 wherein the stages are differing only in the use of hot water instead of cold cleaning liquid.

Step 510 is preceded with moving the lid 210 in an open position, e.g., rolling up the water curtain forming the lid 210, such as opening the bath 206, and lowering the needle block support 134 for the needles 154 to soak in the hot temperature maintained soaking liquid contained by the bath 206. Step 506 consists in emitting ultrasonic waves in the soaking liquid, for the ultrasonic waves to hit the needles and dislodge any residue still stuck to the needles 154 at the time.

After step 510, the needle block support 134 is raised above the elevation of the lid 210, and the lid 210 is closed, preventing cleaning liquid, or water to contaminate the soaking liquid or lower its temperature.

Steps 512 and 514 are essentially repetitions of steps 502 and 504 respectively with hot water to rinse the needles 154.

Step 516, taking place following the cleaning of the interior of the needles 154 with hot water, consists in changing the medium feeding the injection means 216 with air through a controllable valve, for air to be blown with high pressure in the needles 154, drying the needles 154 accordingly.

Step 518 consists in having the ultraviolet light emitters 174 powered while the needles 154 being moved in front of the ultraviolet light emitters 174, thereby having the ultraviolet light (UV light) disinfecting the needles. This step completes sterilization of the needles 154.

Once the step 518 completed, the needle block support 134, if not already in place depending on realizations, is moved to the location where, after the doors 118 being open, an operator will be able to remove the needle blocks 138 from the needle block support 134, the clean needles 154 being ready for utilization.

It is worth mentioning that, throughout the method, the needle block support 134 is moved between its highest position in the elevated 208, mating the injection assembly 226 for cleaning liquid/water/air injection in the needles 154, and its lower position in the bath 206, being soaked in the soaking liquid. According to steps to be performed, the needle block support 134 is repetitively raised and lowered, and the lid 210 is drive between a close position and an open position. Such process allows to avoid the cleaning liquid/water from contaminating the soaking liquid or cooling it down. Accordingly, the consumption of water and/or soaking liquid is limited therethrough, allowing the soaking liquid to be used to clean up a plurality of needle block support 134 holding needles, and it further limits energy consumption used to heat/maintain the soaking liquid at a desired temperature.

Referring back to drawings depicting the apparatus 110, particularly FIGS. 2 to 4, at the beginning of the cleaning process, the needle block support 134 is located at an initial position 142, aka an intermediate position. The first position and neighbor positions are adapted for cleaning step 502, see FIG. 5, where the needles 154 mounted to the needle block support 134 are sprayed with high-pressure cold jets of cleaning liquid ejected from four arrays 218 of nozzles 170, two arrays 218 mounted to the front and two arrays 218 mounted to the back of the housing at two different heights, thereby allowing the needle block support 134 to travel vertically between the arrays 218 and the needles 154 to be sprayed from opposed sides and from different angles to thereby effectively clean the exterior of the needles 154 from sticking residues. Limited spread jets of e.g., 15-30 degrees vertical and horizontal optimize reach of the jets over the whole exterior surface of the needles 154, with the vertical course of needle block support 134 ensuring the needles 154 to be cleaned over their whole height.

In a preferred realization, the needle block support 134 is moved with an alternate vertical movement at least twice for easing the sprayed jets to reach all areas of the needle blocks 138.

Figure 16:
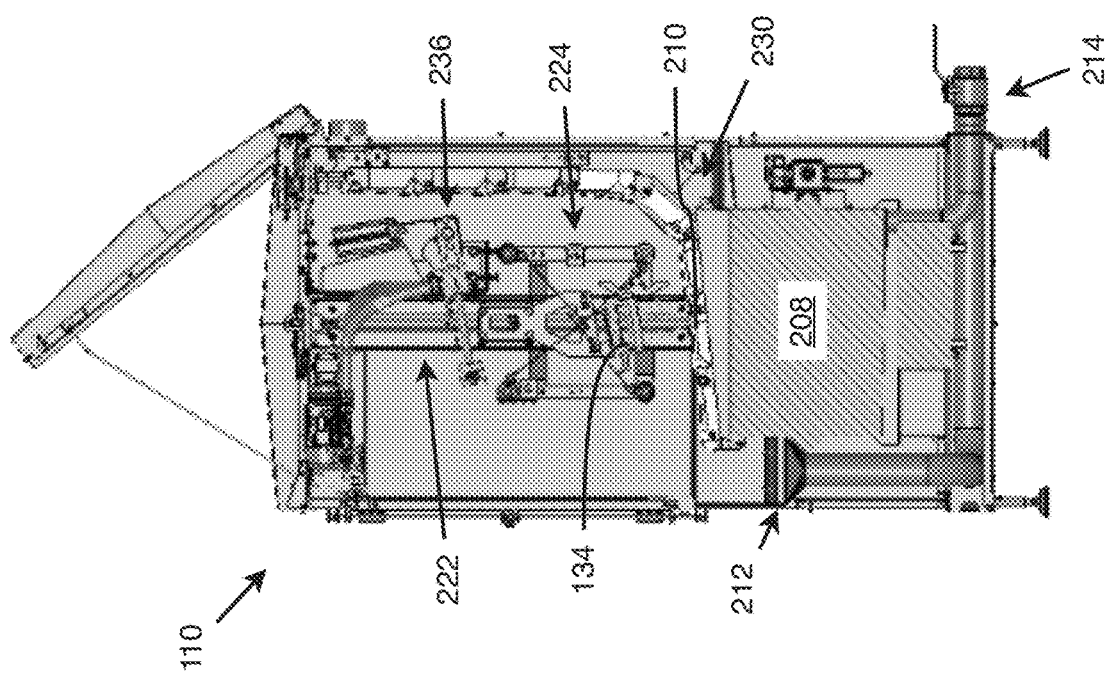
FIG. 16 is a cross-section elevation view according to cross-section lines 16-16 of FIG. 15.

The lid 210 and the gutter assembly 212 depicted on FIG. 16, direct the residue and liquid away from the bath 206, to the gutter assembly 212 leading to an outlet 214.

According to an embodiment, the number of nozzles 170 per array 218 is the double of the number of needle blocks 138 mountable to the needle block support 134. In a preferred realization, all nozzles 170 of a same array 218 are mounted to a common pipe 220, fed together. According to a preferred realization, the pipes 220 are connected to a common inlet.

According to an alternative embodiment, not depicted, controllable valves are used to activate/deactivate arrays of nozzles 170, e.g., in a sequential manner.

According to an alternative embodiment, not depicted, nozzles 170 may be movable along the pipe 220 or controllably orientable during the cleaning process.

Referring particularly to FIG. 3, it is illustrated the cleaning apparatus 110 with the needle block support 134 moved to a second position 150. In the second position, the needle block support 134 is adapted for the injection means 216 of the cleaning apparatus 110 to inject high-pressure cold cleaning liquid, e.g., water through the needles 154 to dislodge and clean residues that may be stuck in the needles 154. In a preferred embodiment, a set of controllable valves 244, FIG. 19, are activated/deactivated to sequentially inject cleaning liquid in the needles 154 of the needle blocks 138, one needle block 138 after another, to clean the interior of all of the needles 154 in a sequential process, limiting the volume of cleaning liquid necessary for the process and decreasing the power requirement of the pump (not depicted per se) used to set the pressure of the cleaning liquid.

Once step 504 is completed, whereby, e.g., hot water is injected in the needles 154, the cleaning apparatus 110 lowers the needle block support 134 followed with lowering and raising the needle block support 134 in an alternate sequence in front of the nozzles 170 used for step 502 during which this alternating course the needles 154 are sprayed with, e.g., hot water, preferably several times, ensuring that the whole height of the needles are hit several times by jets originating from the nozzles 170.

The needle block support 134 is then lowered to the third position 158, aka soaking position, depicted in FIG. 4, for an ultrasonic cleaning process using a series of ultrasound emitters 162 in a soaking liquid, e.g., water bath 166. The needle block support 134 is preferably oscillating a few times while remaining in the water bath 166 for helping removing air bubbles from the needle blocks 138. All the above steps can be repeated several times depending on the amount of residue to be removed.

The needle block support 134 is then raised above the bath 206 in the first position 142 and alternate with the second position 150 for spraying e.g., hot water with the nozzles 170. The needle block support 134 is then moved to the first position 142 for injecting e.g., hot water in the needles 154. Once hot water has been injected, air is blown through the needles 154 to remove remaining water in the needles 154.

The needle block support 134 is then alternating several times between the first position 142 and the second position 150 for the needles 154 to be further cleaned with ultraviolet light emitted by ultraviolet light emitters 174. After, the needle block support 134 is moved to the first position 142 and the needle blocks 138 can be removed from the cleaning apparatus 110.

Figure 6:
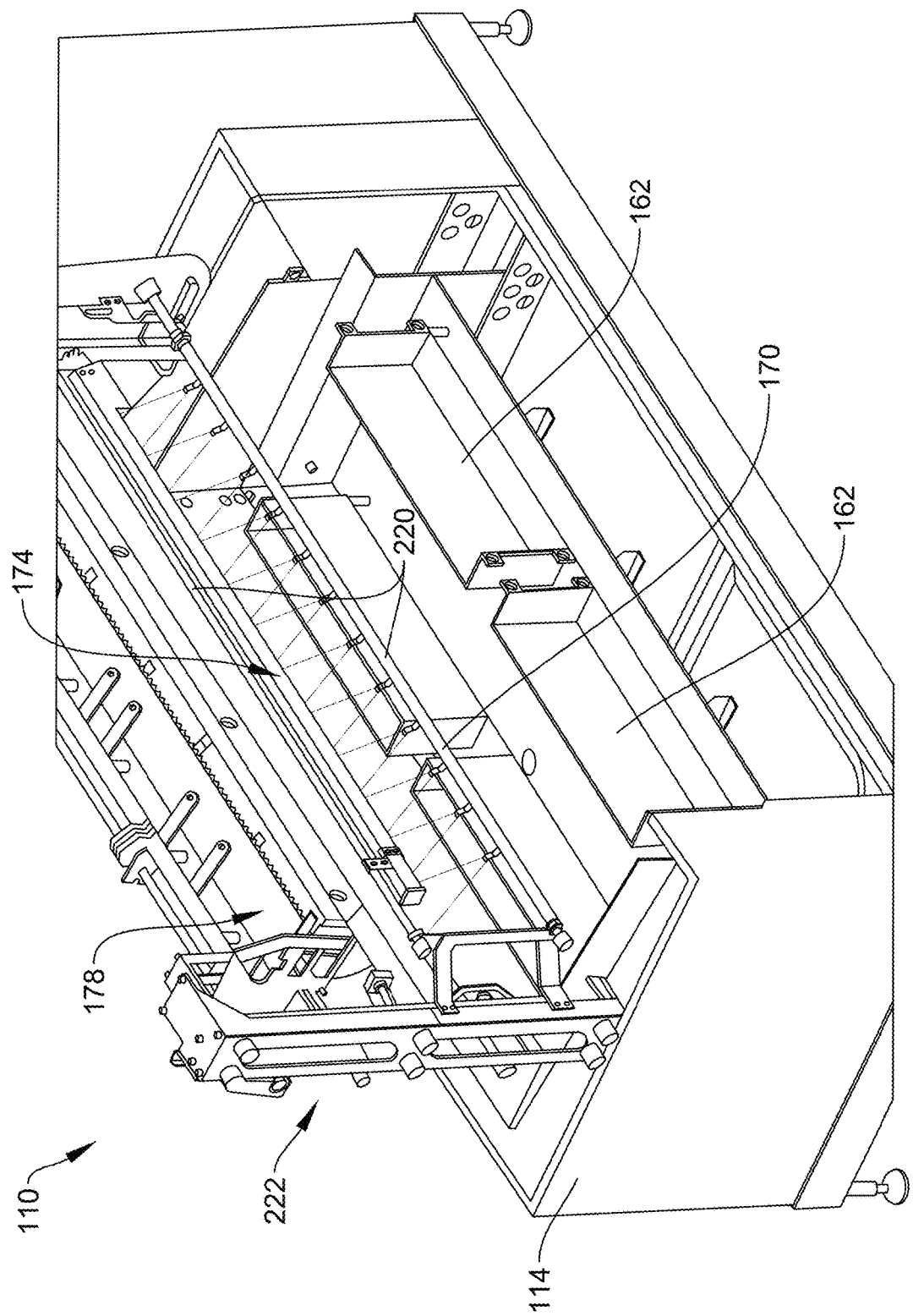
FIG. 6 is a 45-degree front-side perspective view of the needle cleaning apparatus with a lower portion of the housing depicted.
Figure 7:
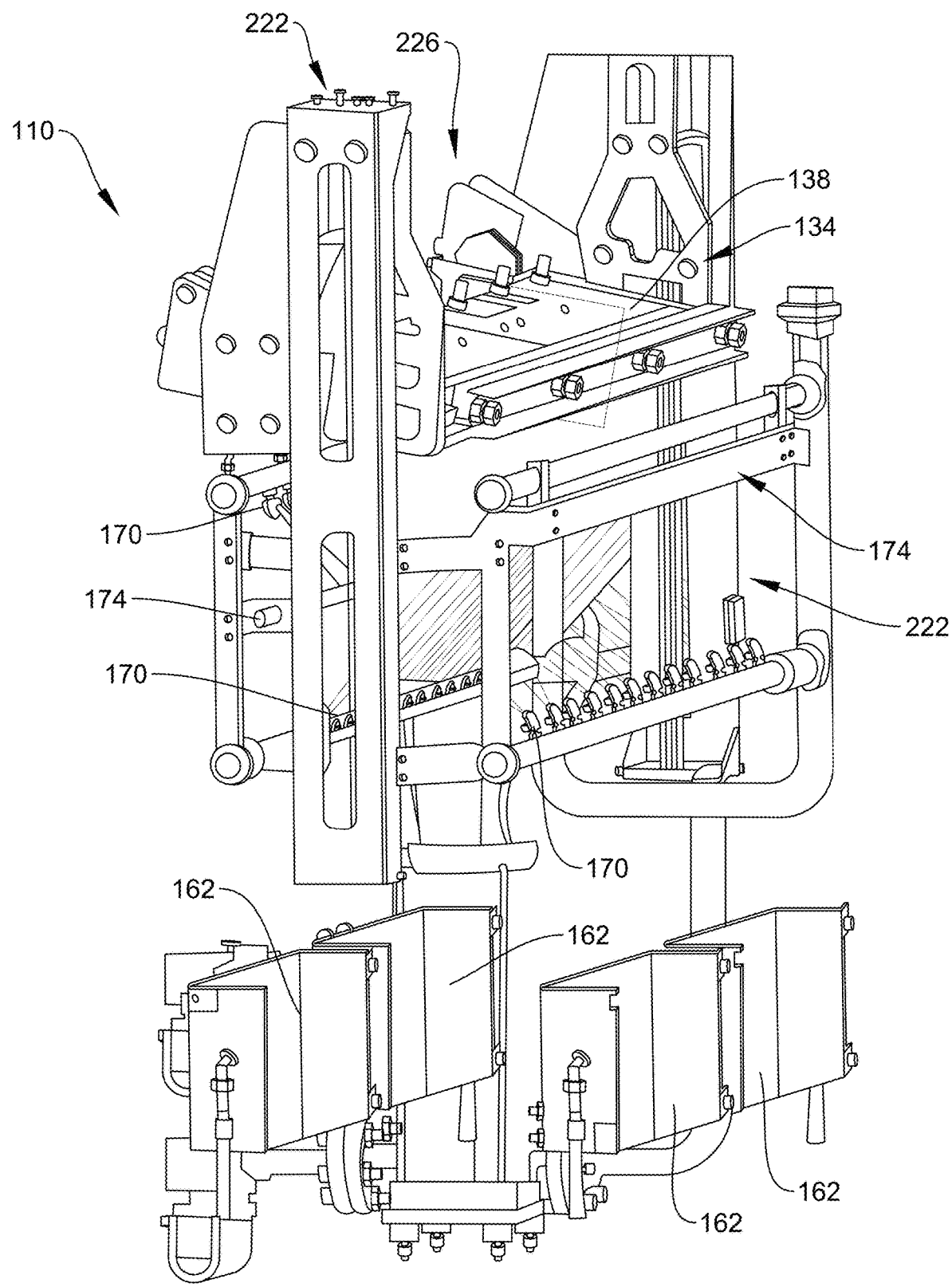
FIG. 7 is a perspective view of components of the spray assembly, the injection assembly, the support driving assembly, ultraviolet emitters, and ultrasound emitters of a needles cleaning apparatus in accordance with an embodiment.

FIG. 6 and FIG. 7 are isometric views of internal components of the cleaning apparatus 110.

FIG. 6 depicts the lower part of the housing 114, ultrasound emitters 162 without the bath 206 depicted, the pipes 220 with nozzles 170 mounted thereto, ultraviolet light emitters 174, and a first side of the support driving assembly 222 for raising and lowering the needle block support 134 during the needle cleaning process.

FIG. 7 depicts components with the housing 114 not depicted, depicting the ultrasound emitters 162 at the bottom without the bath 206 depicted, the spray assembly 224 above, the ultraviolet light emitters 174, the injection assembly 226 and the support driving assembly 222 adapted to raise and lower the needle block support 134.

Figure 8:
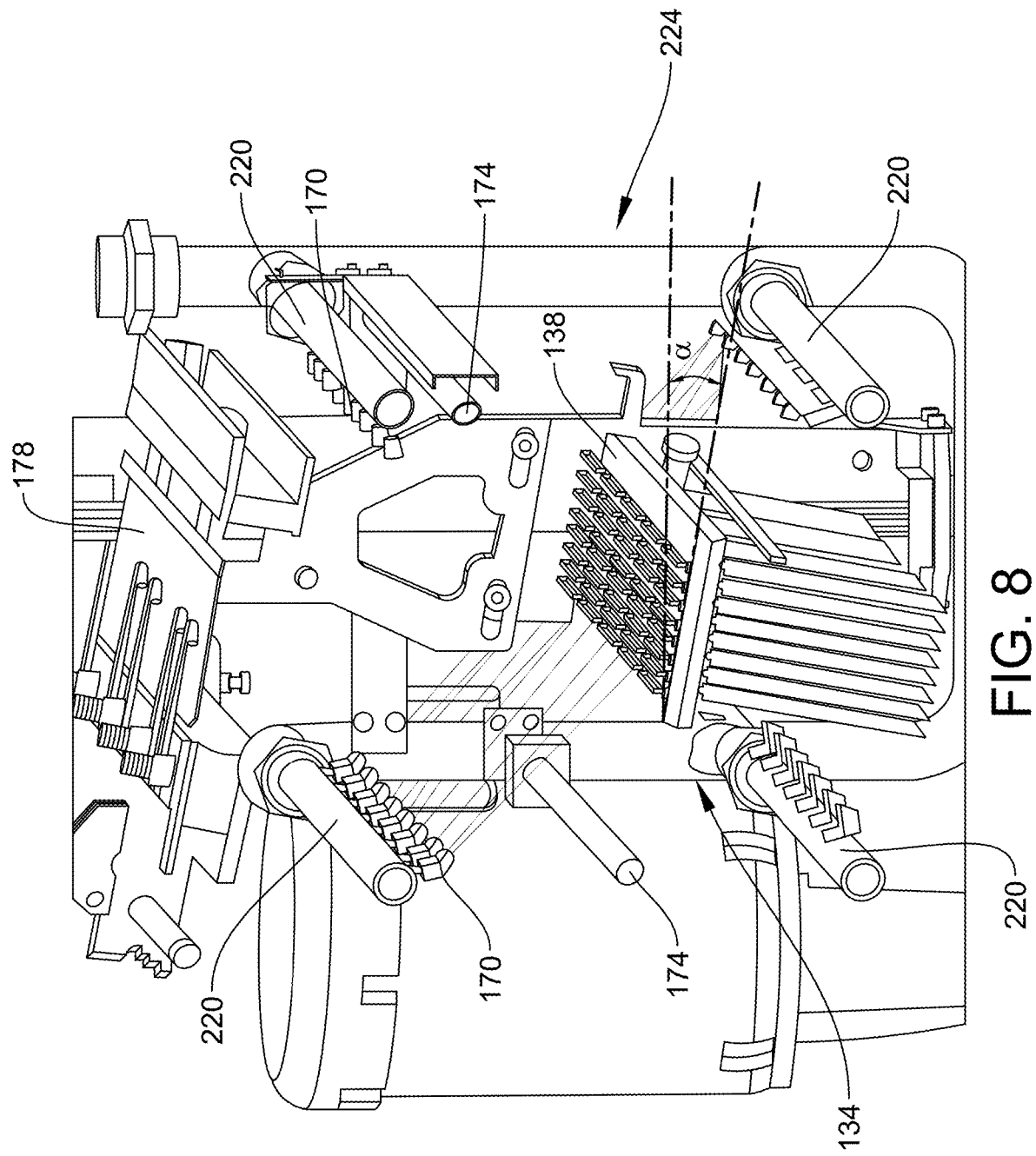
FIG. 8 is a close-up perspective view of components of a needle cleaning apparatus in accordance with an embodiment, depicting a configuration of cleaning jets.
Figure 9:
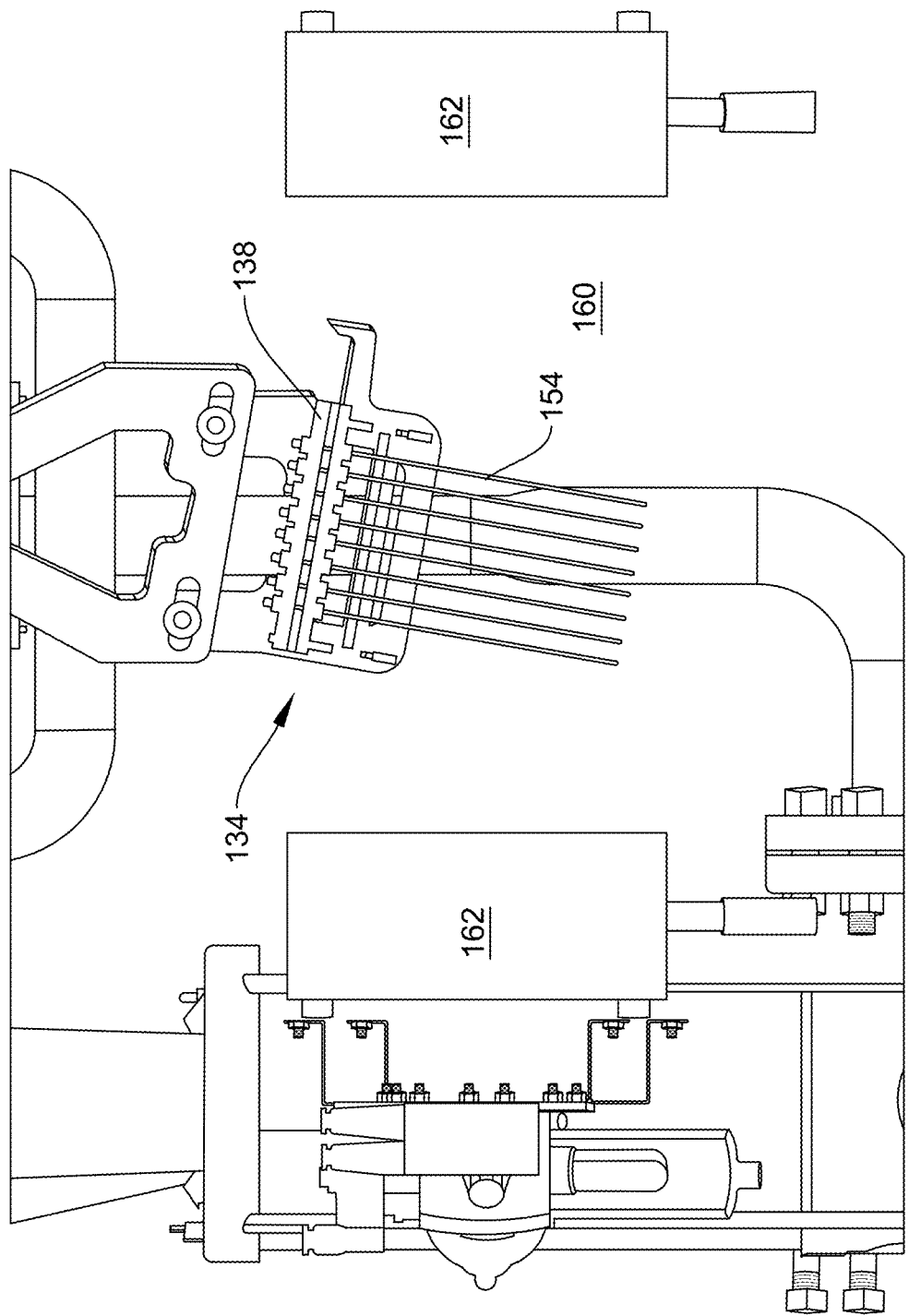
FIG. 9 is a close-up elevated view depicting a needle block in a soaking position in accordance with an embodiment.

FIG. 8 is depicting a closer view of the spray assembly 224 showing spray patterns and the angled position of the needle blocks 138. The angled position of the needle blocks 138 relative to a horizontal reference is intended to flush liquid more easily from the needles 154 and the needle blocks 138 openings therein. A needles retention plate 178 is shown in FIG. 6 (in the soaking position) and is intended to prevent the needles 154 to raise from their needle block 138 when pressure is applied therein in the highest position 150.

Figure 13:
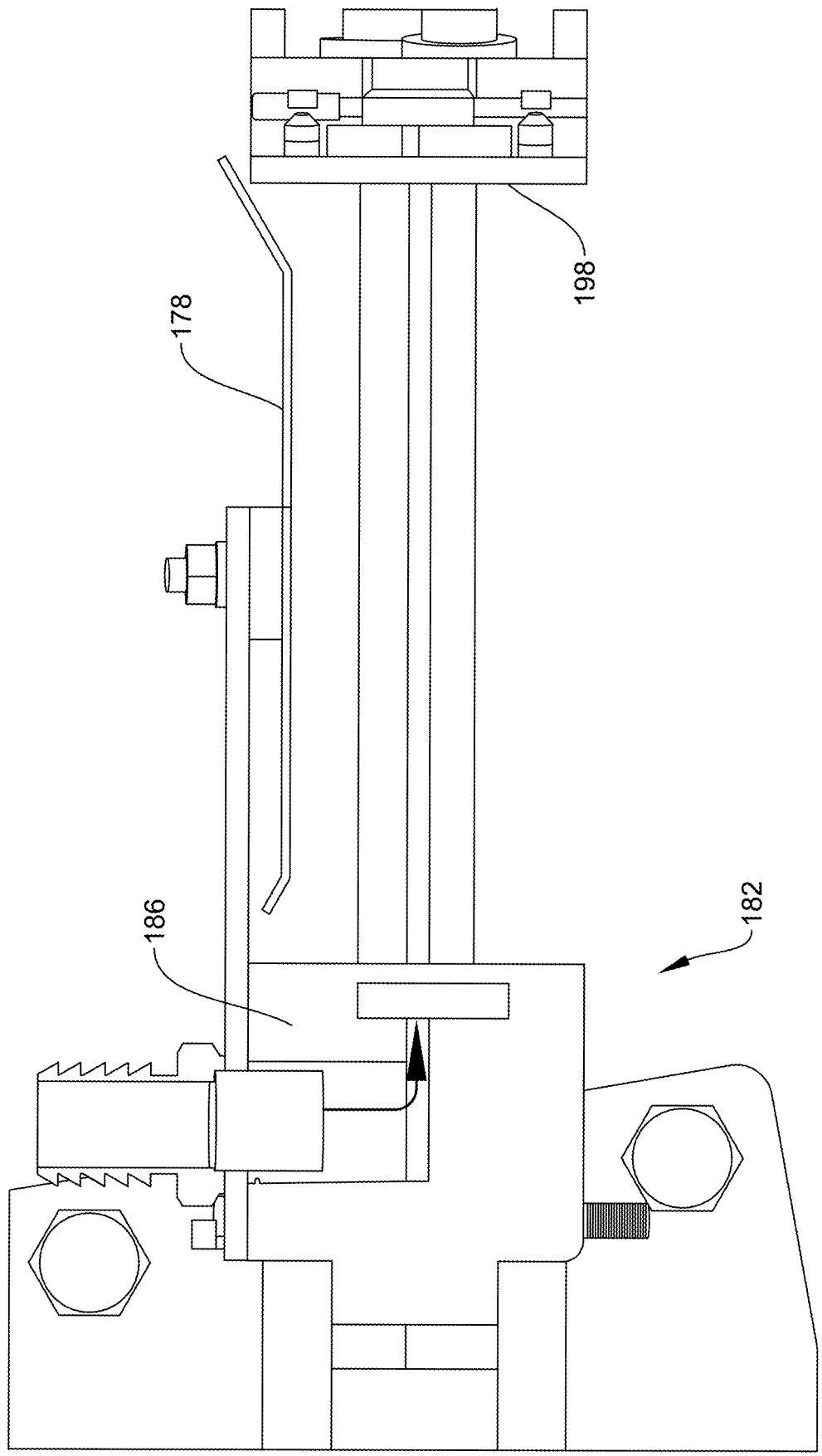
FIG. 13 is a side view of jaws for holding needle blocks in accordance with an embodiment.

FIGS. 8 and 10 throughout FIG. 13 are showing the injection assembly 226 comprising a needle block clamp mechanism 182 used to clamp and secure the needle blocks 138 at an angle α (alpha) of preferably between 10 and 30 degrees from horizontal. The needle block clamp mechanism 182 includes a first jaw 186 with openings therein routing water therein to get in an internal channel 190 in the needle blocks 138 to communicate with an opening 194 in each needle 154 to channel liquid or air down to the tip of the needle 154. It can be appreciated that each needle 154 is secured to the needle blocks 138 and further held on top with the needles retention plate 178. A second jaw 198 is clamping the opposite side of the needle blocks 138 while blocking the internal channel 190. A gasket 202 is added on the contact surface or each jaw 186, 198. The gasket 202 has a taper shape to help alignment of the needle blocks 138 at the right place relative to the clamp mechanism 182.

Figure 14:
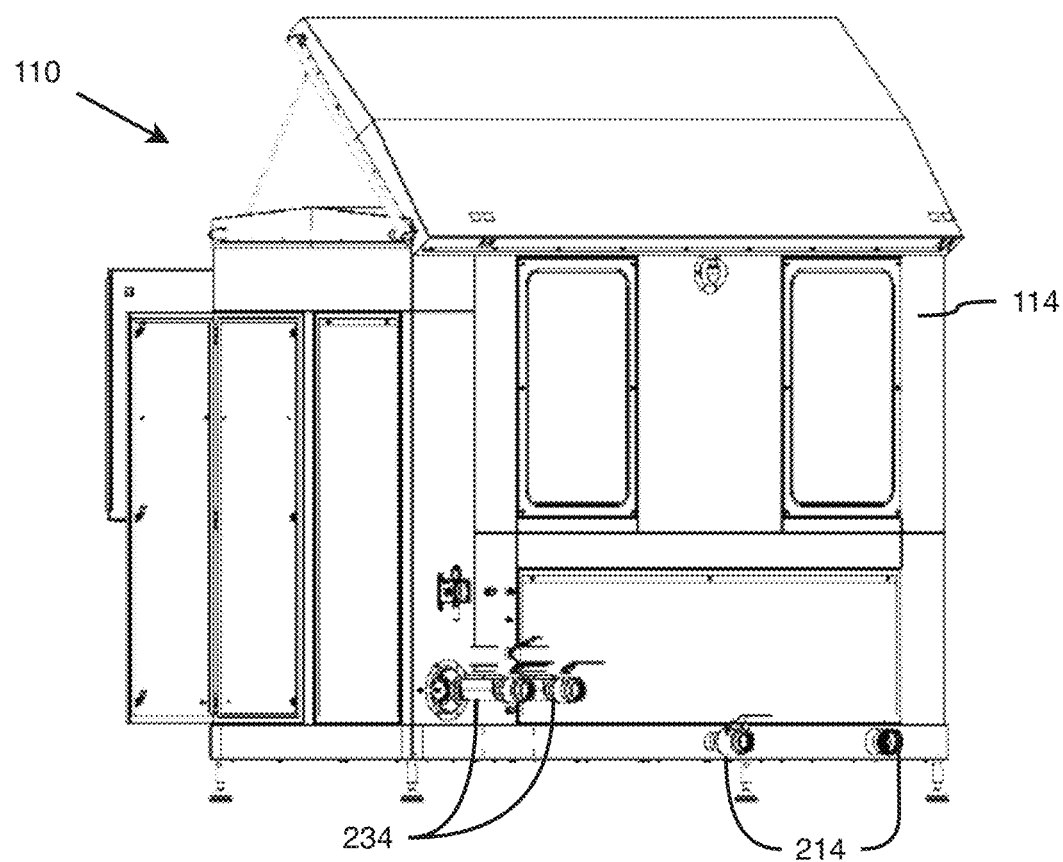
FIG. 14 is a 45-degrees elevation view of the needles cleaning apparatus in accordance with an embodiment.

Referring to FIG. 14, the housing 114 comprises on the back water inlets 234 and outlets 214 for soiled liquid and for emptying the bath 206, FIG. 2.

Figure 15:
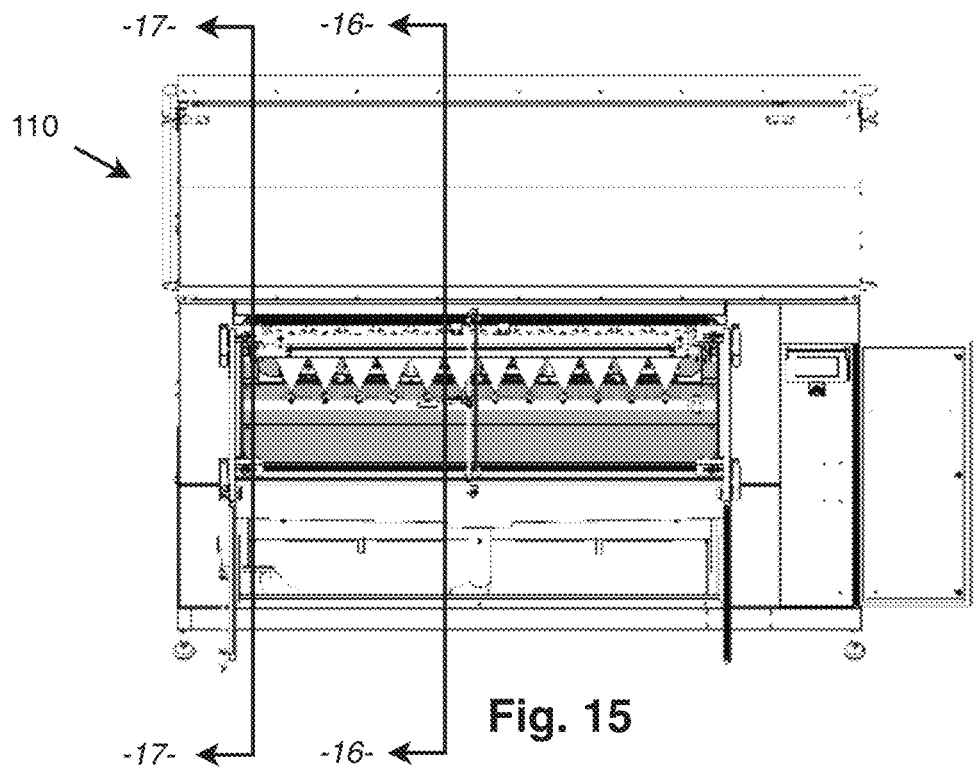
FIG. 15 is a front elevation view of the needles cleaning apparatus with closable doors removed in accordance with an embodiment.
Figure 17:
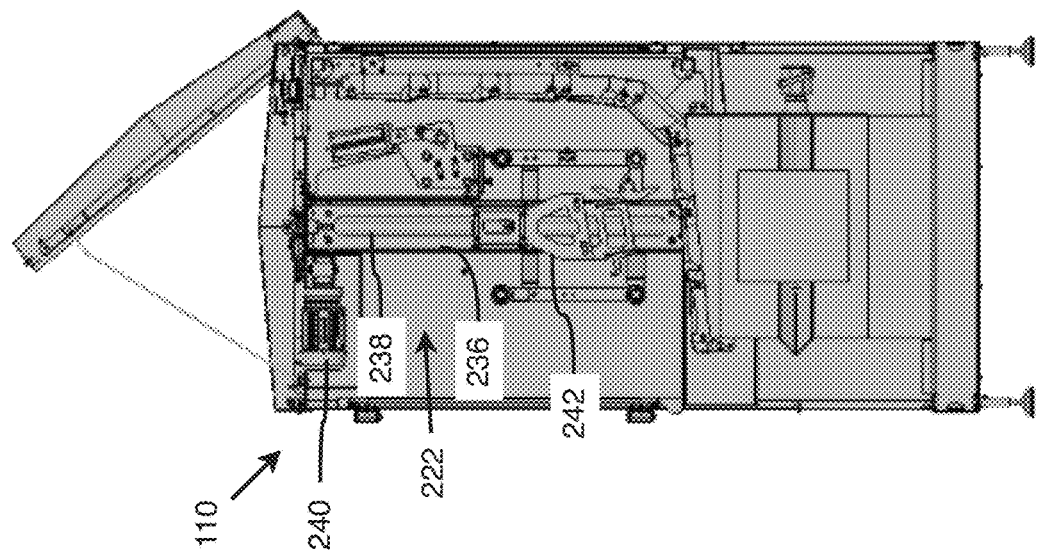
FIG. 17 is a cross-section elevation view according to cross-section lines 17-17 of FIG. 15.

Referring to FIGS. 16, 17 and 19, the cross-section sides elevation views as identified on FIG. 15 and the cross-section rear elevation view identified on FIG. 18 depict components of the spray assembly 224 and one side of the support driving assembly 222. The support driving assembly 222 comprises a vertical rail 236, a linking component 242 connected to the needle block support 134 movable vertically relative to rail 236, a driving element 238, e.g., a screw, powered by a motor 240 preferably mounted on the top, driving the linking component 242 into vertical movements of the needle block support 134. FIG. 16 depicts the lid 210 in the closed position, isolating the elevated area 208 from the bath 206. The lid 210, made of inter-connected sections, is movable rearward and upward into an open position. Slope of the lid 210 in the closed position leads liquid falling on the lid 210 to flow in the gutter assembly 212 located in front of the bath 206, extending over the width of the bath 206, and comprising components extending downward and rearward to flush the liquid through an outlet 214. Controllable valves 244 allows to selectively inject in the needle blocks 138 when the injection assembly 226 is in operation.

Figure 20:
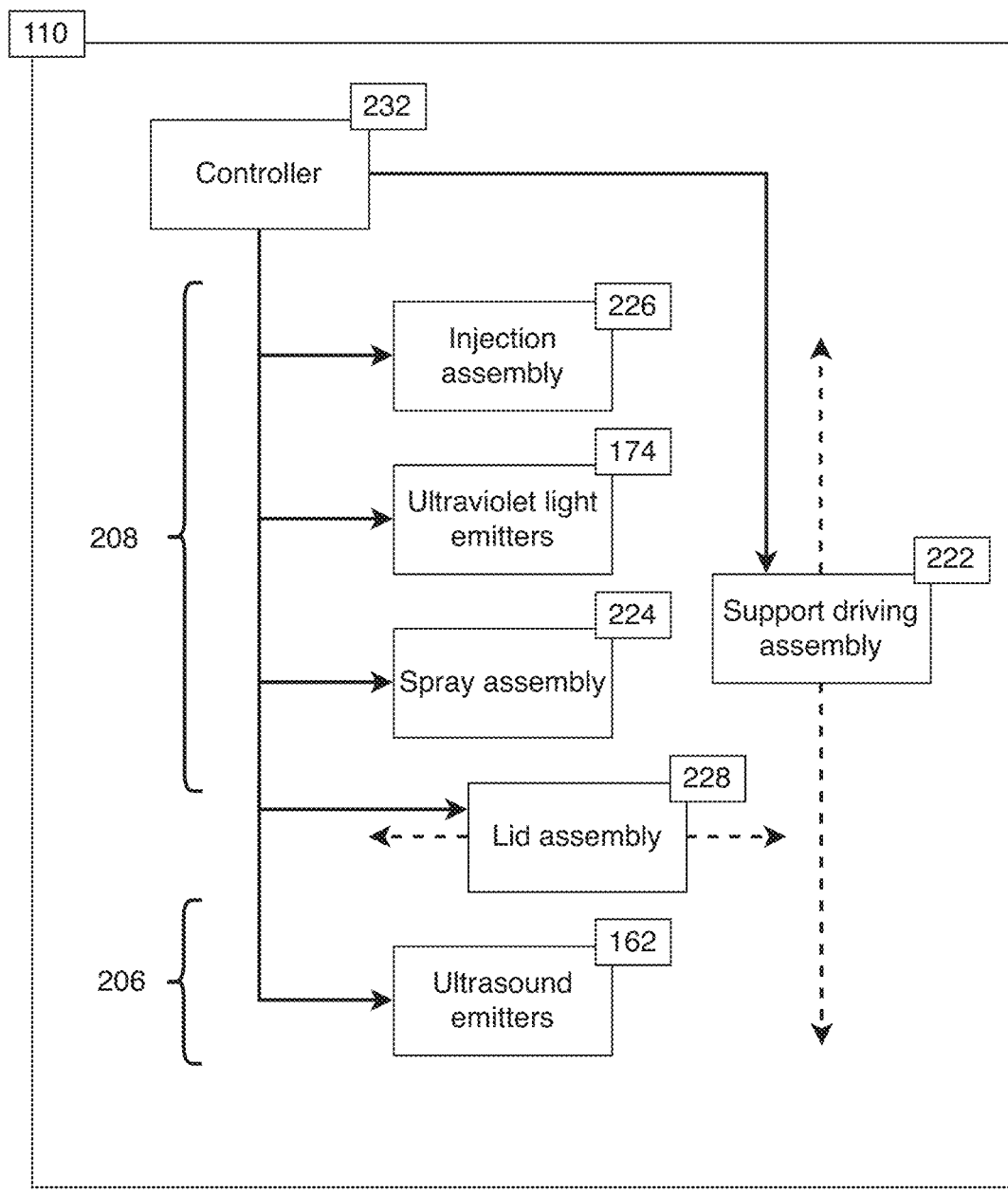
FIG. 20 is a block diagram depicting components of a needles cleaning apparatus in accordance with an embodiment.

Referring to FIG. 20, the cleaning apparatus 110 comprises an injection assembly 226, ultraviolet light emitters 174, a spray assembly 224 in an elevated area 208. A lid assembly 228, comprising the lid 210 and lid driving assembly 230, FIG. 16, controllably isolates the elevated area 208 from the bath 206 located below the lid 210 when closed. Ultrasound emitters 162 are adapted to emit ultrasonic waves to be transmitted to the needles in the bath 206. A support driving assembly 222 is adapted to move the needle block support 134 between stations where assemblies 222, 224 and emitters 174, 162 operate. A controller 232 operatively connected to the external control display 130, FIG. 1, controls the operations of the assemblies 222, 224 and the emitters 174, 162.

It is worth mentioning that the last block diagram of FIG. 20 with accompanying description, while limited to broad components, intend to also cover more specific automated sub-components, e.g., controllable valves, position detection sensors, pression sensors, temperature sensors, gauges, heaters, etc. and manual component, e.g., inlet valves, draining valves, etc.

It is worth mentioning that the cleaning cycle described herein is exemplary only. General expressions such as cleaning liquid, rinsing liquid and soaking liquid are used as functional description and are not intended to limit their nature and/or characteristics. The terms/expressions hot/cold and high pressure are also functional. They are intended to be understandable by a person skilled in the art in light of the following exemplary operational characteristics.

In the exemplary cleaning cycle, high pressure jets refer to jets of about 200 PSI (pound per square inch). High pressure injecting pressure refers to a pressure of about 225 PSI. Simple cleaning cycle, either injection cycle than spray cycles are completed in between 20 second and 2 minutes, and preferably between 30-40 seconds, with the number of repetitions on single cycle to perform a complete cycle varying between 1 and 5, and preferably 2. Ultrasound processing consists in cycles of typically between 15 minutes and 2 hours, preferably about 45 minutes, with a number of repetitions of between 1 and 5, and preferably 2. Drying of the needles 154 with air blown is performed with cycles of between 15 seconds and 2 minutes, preferable of about 30 seconds, with a number of repetitions between 1 and 2, and preferably 1 with an air pressure of about 60 to 120 PSI. Ultraviolet light processing takes between 1 and 15 minutes, and preferably of about 5 minutes of preferably UV-C light.

Cold liquid refers to temperature of water from common source, e.g., the tap, without additional temperature treatments, with or without additives. Hot water refers to water heated to a temperature of preferably between 35 and 70 degree Celsius, and preferably a temperature of about 50 degree Celsius.

Cleaning liquid is preferably one of water or water mix a non-foaming detergent. Cleaning water may vary between cleaning processes in its nature, e.g., water vs. solution, and in the concentration of additives. The same applies based on the nature of the residues to clean off the needles.

Rinsing liquid is preferably water.

Soaking water is preferably water with or without additives. Ultrasound emitters are typically four (4) 1000 Watts emitters mounted to the side of the bath of about 100 gallons operating with ultrasonic waves of between 25 to 170 Khz.

The whole needle cleaning process typically involves a liquid consumption between 300 and 1000 liters, and preferably about 500 liters, excluding the content of the bath kept from one cleaning operation to the other, until the soaking water becomes too contaminated.

These skilled in the art would understand that the herein-provided values are for teaching purpose, with the values changing based on, e.g., the number of needle blocks cleaned at the same time, the pressure applied, the temperature of the liquids, the volume of the bath, etc.

The description and the drawings that are presented above are meant to be illustrative of the present invention. They are not meant to be limiting of the scope of the present invention. Modifications to the embodiments described may be made without departing from the present invention, the scope of which is defined by the following claims:

The invention claimed is:

1. A meat injection needles cleaning apparatus for cleaning needles from residues, the needles having an exterior surface, a top and a tip, the apparatus comprising:
a housing defining a closeable room comprising a bath for containing a soaking liquid, an elevated area above the bath;
a movable lid:
a lid driving assembly, wherein the lid driving assembly is moving at least partially vertically the movable lid within the housing between a cover position wherein the movable lid at least partially isolates the bath and the elevated area from one another, preventing liquid dripping from the elevated area to enter the bath and to mix with the soaking liquid of the bath, and an open position wherein the lid allows the liquid dripping from the elevated area to enter the bath and mix with the soaking liquid;
a support for mounting the needles thereto in an oblique position relative to surface of the soaking liquid, the top upraised relative to the tip;
a support driving assembly driving, at least partially, vertically the support in the housing while keeping the needles in the oblique position, the support driving assembly driving the support between a) a soaking position wherein the needles are lowered in the bath, and b) at least one elevated position wherein the needles are raised in the elevated area at least partially above the bath, and wherein the needles are outside the soaking liquid when soaking liquid remains in the bath; and;
a cleaning assembly cleaning the needles in the elevated area, wherein the cleaning assembly comprises at least one of a) a spraying nozzle assembly spraying the exterior surface of the needles with one of a cleaning liquid or water, and b) at least one injection assembly injecting the needles with one of the cleaning liquid or water.

2. The apparatus of claim 1, further comprising at least one ultrasound emitter for emitting ultrasonic waves in the soaking liquid.

3. The apparatus of claim 1, further comprising ultraviolet light emitters.

4. The apparatus of claim 1, wherein the injection assembly is operable to selectively inject liquid and air in the needles.

5. The apparatus of claim 1, wherein the cleaning assembly comprises a spray assembly comprising at least two nozzle arrays each comprising at least one nozzles, with the support being adapted to travel between the at least two nozzle arrays to align the needles to a single one of the nozzle arrays at a time.

6. The apparatus of claim 1, further comprising a gutter assembly, wherein the lid when in the cover position redirects liquid directly from the elevated area into the gutter assembly.

7. The apparatus of claim 1, wherein the lid comprises a plurality of interconnected sections, the plurality of interconnected sections being flexibly adjoined to one another.

8. The apparatus of claim 1, wherein the support driving assembly is adapted to move the support in front of the cleaning assembly during operation of the cleaning assembly.

9. The apparatus of claim 1, wherein the support driving assembly comprises a pair of rails on which is mounted the support.

10. A meat injection needles cleaning apparatus for cleaning needles from residues, the needles having an exterior surface, a top and a tip, the apparatus comprising:
- a housing comprising a bath for containing a soaking liquid and an elevated area outside above the bath;a support for mounting the needles thereto in an oblique position relative to surface of the soaking liquid, the top upraised relative to the tip;
- a support driving assembly driving the support between a) a first position in the bath, b) a second position in the elevated area, and c) a third position in the elevated area;
- a cleaning assembly cleaning the needles in the elevated area, wherein the cleaning assembly comprises a) a spraying nozzle assembly spraying upwardly the exterior surface of the needles with one of a cleaning liquid or water, and b) an injection assembly injecting the needles with one of the cleaning liquid or water;
- ultrasound emitters located in the bath, the ultrasound emitter emitting ultrasonic waves in the soaking liquid of the bath reaching the needles when in the bath;
- ultraviolet light emitters submitting the needles to ultraviolet light in the elevated area, wherein the support driving assembly driving the support between the second position and the third position when the needles are continuously submitted to the ultraviolet light; and
- a controller
  i) for selectively driving the support between the first position, the second position, and the third position;
  ii) for selectively activating the cleaning assembly, the ultrasound emitters, and the ultraviolet light emitters.

11. The apparatus of claim 10, wherein the injection assembly is operable to selectively inject liquid and air in the needles.

12. The apparatus of claim 10, wherein the spraying nozzle assembly comprising at least two nozzle arrays each comprising at least one nozzle, with the support driving assembly driving the support with the needles mounted thereto between about a first one of the nozzle arrays and a second one of the nozzle arrays.

13. The apparatus of claim 1, wherein the support is adapted for mounting the needles oblique relative to surface of the soaking liquid in the bath.

14. The apparatus of claim 1, wherein the spray nozzle assembly sprays jets that are oblique relative to surface of the soaking liquid in the bath.

15. The apparatus of claim 1, wherein the housing comprises a door opening to access the elevated area above the bath, with the needles being inserted therethrough.

16. The apparatus of claim 1, further comprising a controller, the cleaning assembly further comprises a valve assembly fluidly controlled by the controller, the valve assembly being connected to a hot-water inlet and a cold-water inlet, wherein the controller is adapted to selectively control temperature of the water fed to the spraying nozzle assembly.

17. The apparatus of claim 1, wherein the lid driving assembly comprises a rail located within the housing, wherein the movable lid is driven at least partially vertically following the rail within the housing.

18. The apparatus of claim 1, wherein the spraying nozzle assembly is spraying the cleaning liquid or water upwards towards the needles.

19. The apparatus of claim 10, further comprising a movable lid and a lid driving assembly,
- wherein the lid driving assembly is moving at least partially vertically the movable lid within the housing between a cover position wherein the movable lid at least partially isolates the bath and the elevated area from one another, preventing liquid dripping from the elevated area to enter the bath and to mix with the soaking liquid of the bath, and an open position wherein the lid allows the liquid dripping from the elevated area to enter the bath and mix with the soaking liquid.

20. The apparatus of claim 19, further comprising a gutter assembly, wherein the lid when in the cover position redirects liquid firectly from the elevated area into the gutter assembly.

21. The apparatus of claim 19, wherein the lid comprises a plurality of interconnected sections, the plurality of interconnected sections being flexibly adjoined to one another.

* * * * *